United States Patent [19]

Kesson

[11] Patent Number: 4,461,165
[45] Date of Patent: Jul. 24, 1984

[54] METHOD OF AND APPARATUS FOR MONITORING CONCENTRATION OF GAS IN A LIQUID

[75] Inventor: James Kesson, Edinburgh, Scotland

[73] Assignee: Scottish & Newcastle Breweries Limited, Edinburgh, Scotland

[21] Appl. No.: 275,964

[22] Filed: Jun. 22, 1981

[30] Foreign Application Priority Data

Jun. 27, 1980 [GB] United Kingdom ............... 8021127

[51] Int. Cl.³ .............................................. G01N 7/10
[52] U.S. Cl. ........................................ 73/19; 73/61 R
[58] Field of Search ................................. 73/19, 61 R

[56] References Cited

U.S. PATENT DOCUMENTS

| 3,681,026 | 8/1972 | Holden | 73/19 X |
| 3,866,460 | 2/1975 | Pearce, Jr. | 73/19 |
| 3,871,228 | 3/1975 | Weiss | 73/19 |

FOREIGN PATENT DOCUMENTS

| 1452574 | 10/1976 | United Kingdom . |
| 1494441 | 12/1977 | United Kingdom | 73/19 |

Primary Examiner—S. Clement Swisher
Assistant Examiner—Joseph W. Roskos
Attorney, Agent, or Firm—Mason, Fenwick & Lawrence

[57] ABSTRACT

A method of and apparatus for monitoring the concentration of gas in a liquid includes a semi-permeable diaphragm across the face of which the liquid flows. Gas contained in the liquid permeates through the diaphragm into a chamber and the pressure within the chamber is measured. This pressure is representative of the concentration of gas in the liquid and permits control of the quantity of gas injected.

9 Claims, 4 Drawing Figures

METHOD OF AND APPARATUS FOR MONITORING CONCENTRATION OF GAS IN A LIQUID

BACKGROUND OF THE INVENTION

This invention relates to a method of and to apparatus for monitoring the concentration of a gas in a liquid.

The invention has particular application in the measuring and control of the content of carbon dioxide gas in beer and lager. The $CO_2$ content in beer or lager is important in that the quality of the beer or lager is determined to some extent by the gas content which varies according to the eventual packaging of the beer. For example, canned and bottled beer require a higher gas content than kegged beer destined for draught.

Systems are known for measuring the $CO_2$ content in beer but involve the use of a gas analyser which evaluates the $CO_2$ volume concentration of a sample of the beer.

Such systems are to some extent impractical in so far as a delay neccessarily exists from the time the sample is taken to the time the results of the analysis are known and suitable adjustment of the quantity of $CO_2$ injected is effected. Additionally, gas analysers are expensive pieces of equipment and it is not feasible to provide each production line in a large bottling plant with its own analyser, thus resulting in further delay before control can be carried out.

SUMMARY OF THE INVENTION

It is an object of the present invention to obviate or mitigate the drawbacks and inconveniences of hitherto proposed systems and to provide a relatively economic means whereby the concentration of gas in a liquid may be monitored and controlled.

According to the present invention there is provided a method of monitoring the concentration of gas in a liquid comprising passing said liquid across a semi-permeable membrane in order that gas in the liquid may permeate through the membrane, and measuring the pressure of the permeated gas.

Preferably, said measured pressure is corrected for the temperature of the liquid.

Further according to the present invention there is provided apparatus for monitoring the concentration of gas in a liquid comprising a semi-permeable membrane fixed in a housing and arranged to have one side in contact with said liquid, means defining a chamber on the side of said membrane remote from the liquid, and means for determining the pressure in said chamber.

Preferably, the pressure of the permeated gas is used to generate a pressure representative signal which is passed to a control unit which in turn produces a control signal to control the quantity of gas injected into the liquid.

DESCRIPTION OF THE DRAWINGS

Embodiments of the present invention will now be described, by way of example, with reference to the accompanying drawings, in which.

DESCRIPTION OF THE PREFERRED EMBODIMENTS

Figure 1:
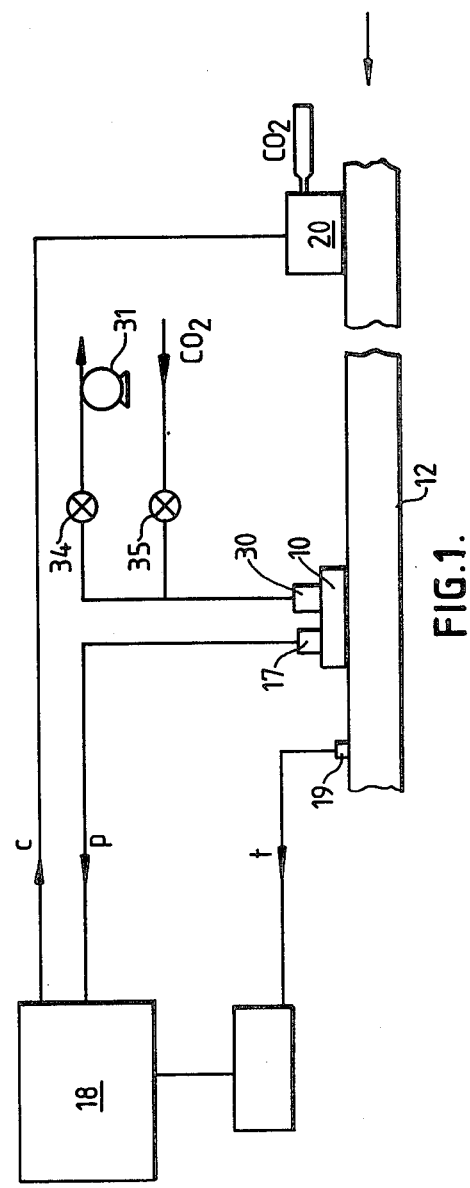
FIG. 1 shows schematically one embodiment of apparatus made in accordance with the present invention.
Figure 2:
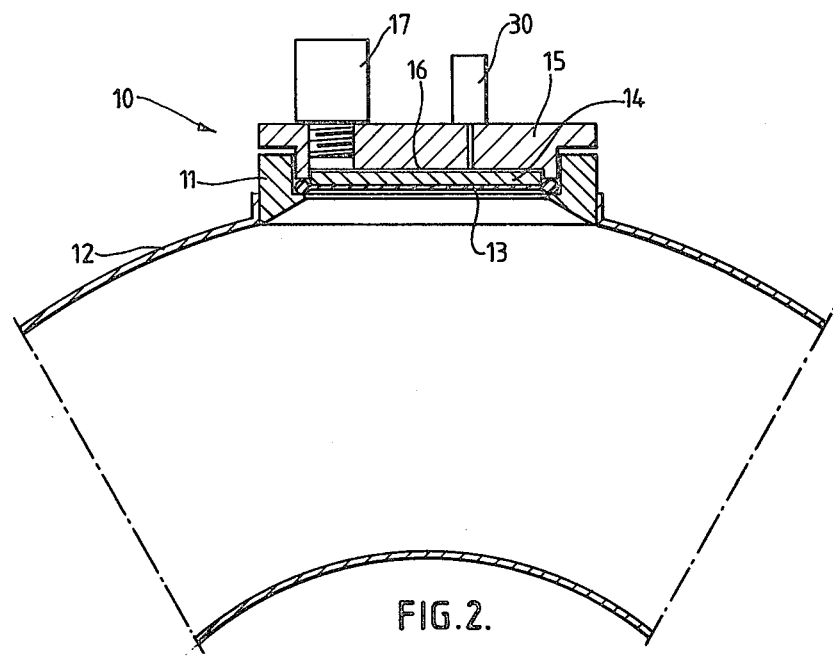
FIG. 2 is a sectional view of a basic embodiment of the pressure measuring device of the apparatus of FIG. 1 fitted to a pipe.
Figure 3:
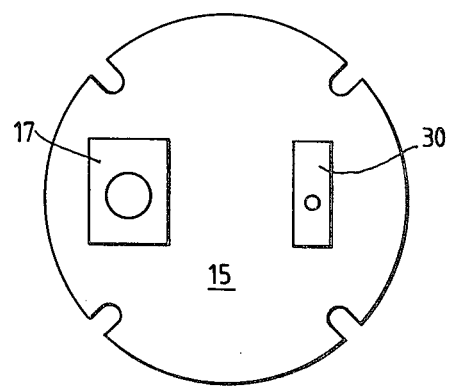
FIG. 3 is a top plan view of the top cover of the device of FIG. 2.

Referring to the drawings, apparatus for monitoring the gas concentration in a liquid comprises a pressure measuring device 10 in the form of a housing 11 fitted in a pipe 12 along which flows the liquid to be monitored. The housing 11 carries a semipermeable membrane in the form of a silicone rubber diaphragm 13. To prevent undue distention of the diaphragm 13 a gas-porous support disc 14 which can conveniently be formed of sintered steel is interposed between the diaphragm 13 and a top cover 15. The top cover 15 defines a chamber 16 into which gas contained in the liquid flowing along the pipe 12 diffuses. Thus the pressure in the chamber is representative of the concentration of gas in the liquid. As the concentration of gas increases, the partial pressure of the gas in the liquid increases and more gas diffuses into the chamber 16 causing an increase in the pressure within the chamber. Similarly, as the concentration of gas decreases, the partial pressure decreases and gas diffuses out of the chamber 16 into the liquid causing a decrease in the pressure within the chamber.

The pressure in the chamber 16 is measured by means of a pressure transducer 17 which passes a pressure representative electrical signal (p) to a control and display unit 18. A temperature representative electrical signal (t) is derived from a temperature probe 19 and passed to the control unit 18. The pressure signal (p) is corrected for temperature and the value of gas concentration in the liquid is evaluated and displayed. Preferably, the gas concentration value is compared with a preset value and a control signal (c) is generated.

Should the concentration of gas fall outside the desired preset limits appropriate adjustment of the gas injection system 20 is carried out. Such adjustment is carried out automtically through an injection control unit 20 which receives the control signal (c) from the device control unit 18.

Thus, by virtue of a flow of gas through diaphragm 13 into and out of the chamber 16 equilibrium is maintained between the pressure of the gas in the chamber 16 and the partial pressure of the gas in the liquid, this partial pressure being representative of the concentration of gas in the liquid.

To avoid inaccurate readings, the chamber 16 is evacuated at start-up by means of a vacuum pump 31 through a solenoid operated vent valve 30 fitted to the top cover 15. Also, gas, for example $CO_2$ from a supply 33 may be introduced into the chamber 16 by appropriate operation of the valve 30 and of auxiliary solenoid valves 34 and 35.

Figure 4:
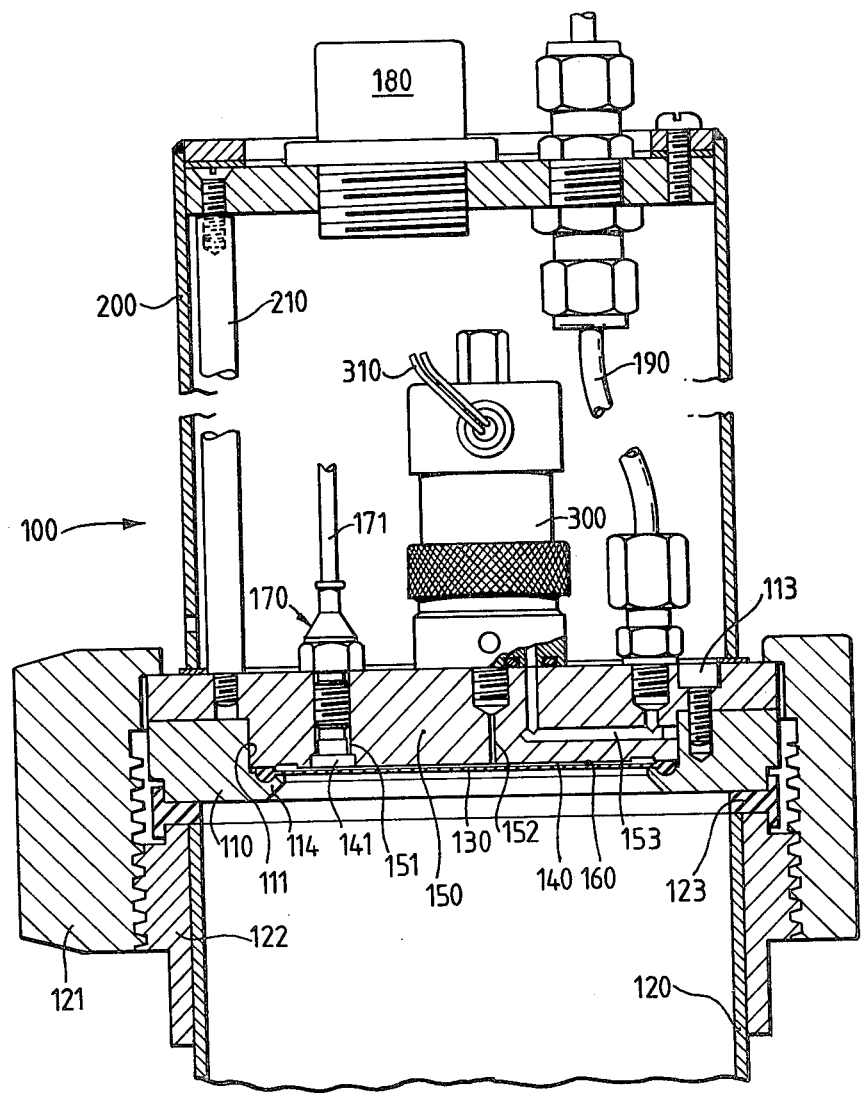
FIG. 4 is a sectional view, in elevation, of an improved embodiment of the pressure measuring device of the apparatus of FIG. 1.

Referring now to FIG. 4 of the drawings, there is illustrated an improved embodiment of apparatus made in accordance with the present invention.

In the drawings, a pressure measuring device 100 has a base 110 having a circular opening 111 in which there is received a main body 150. The main body 150 is held in the opening 111 by screws 113. The resultant cylindrical combination is illustrated fixed to a branch pipe 120 by means of a ring nut 121 which cooperates with a threaded portion 122 of the pipe 120. A suitable seal 123 is provided and the pipe 120 communicates with a main pipe along which flows the liquid to be monitored.

A semi-permeable membrane in the form of a silicone rubber diaphragm 130 is held between the peripheral edge of the lower face of body 150 and a circular ridge 114 of the base 110.

A chamber 160 is thus defined between the lower face of the body and the upper face of the diaphragm 130. A wire mesh screen 140 within the chamber 160 is interposed between these two faces and serves to avoid any distortion of the diaphragm.

The main body 150 is provided with a first through orifice 151 into which there is fitted a pressure transducer 170 which communicates with the chamber 160 via a sintered bronze insert 141. A pressure representative signal from the transducer 170 is passed to a control unit through suitable wiring 171 fed to a connector 180.

A second through orifice 152 serves to connect the chamber 160 with one port of a solenoid operated valve 300. The valve 300 is operated by means of wiring 310 connected to connector 180. The other port of the valve 300 connects with passageways 153 drilled in the body 150 which in turn connects with pipe 190. The pipe 190 connects with a vacuum pump and supply of gas, for example, $CO_2$, whereby the chamber 160 may be evacuated, vented to atmosphere, or charged with gas, thereby to increase the accuracy of measurement of the device.

To protect the transducer 170, valve 300 and pipe 190, the device is provided with a hollow cylindrical cover 200 supported by pillars 210 and fixed on the body 150.

The device of FIG. 4 operates as follows.

As liquid flows from the main pipe into branch pipe 120, gas contained in the liquid diffuses through the diaphragm 130 into and out of the chamber 160. As the concentration of the gas within the liquid changes, the partial pressure of the gas in the liquid changes proportionally. This change results in a pressure differential across the diaphragm 160 and gas flows into or out of the chamber until equilibrium is achieved. Thus the pressure in the chamber, as detected by the transducer 170 is representative of the concentration of gas in the liquid.

The signal from the transducer 170 can thus be used to control the quantity of the gas injected into the liquid and therefore a desired level of concentration can be achieved.

Accordingly, there has been described a method of and apparatus for monitoring the concentration of gas in a liquid. The apparatus provides on-line control of the quantity of gas in the liquid.

Modifications and improvements may be incorporated without departing from the scope of the invention.

What is claimed:

1. A method of controlling the concentration of gas in a liquid comprising:
    passing said liquid across a semi-permeable membrane in order that gas in the liquid may permeate through the membrane into a measuring chamber,
    generating a pressure representative electrical signal representative of the pressure of the permeated gas in said chamber,
    comparing said pressure representative signal with an electrical signal representative of a desired concentration of gas in the liquid to generate a control signal, and
    using said control signal to control the quantity of said gas injected into the liquid thus to maintain constant the concentration of gas in the liquid.

2. A method as claimed in claim 1 wherein the measured pressure is corrected for temperature.

3. Apparatus for controlling the concentration of gas in a liquid, comprising:
    a housing for fitment to a container or conduit carrying said liquid;
    a chamber in said housing;
    a semi-permeable membrane fixed in said housing, one side of said membrane being arranged to be in contact with said liquid and the other side of said membrane forming a wall of said chamber so that gas in said liquid may permeate through said membrane into said chamber;
    means for generating an electrical pressure representative signal representative of the pressure of said gas within said chamber;
    means for comparing said pressure representative signal with an electrical signal representative of a desired concentration of said gas in the liquid to generate a control signal; and
    means responsive to said control signal to control the quantity of said gas injected into the liquid thus to maintain constant the concentration of said gas in the liquid.

4. Apparatus as claimed in claim 3 wherein said semi-permeable membrane is formed of a silicone rubber diaphragm.

5. Apparatus as claimed in claim 3 wherein the membrane is supported by a gas porous support member.

6. Apparatus as claimed in claim 5 wherein the gas porous support member is in the form of a sintered steel disc.

7. Apparatus as claimed in claim 5 wherein the gas porous support member is formed of wire mesh.

8. Apparatus as claimed in claim 3 and including solenoid operable valve means on the housing and communicating with the chamber whereby the chamber may be vented to atmosphere, evacuated, or charged with gas.

9. Apparatus as claimed in claim 3 and including means for measuring the temperature of the liquid and correcting the pressure representative signal accordingly.

* * * * *